(12) United States Patent  (10) Patent No.: US 8,975,413 B2
Jung et al.  (45) Date of Patent: Mar. 10, 2015

(54) METHOD OF PREPARING RADIOISOTOPE NANOSTRUCTURE WITH LIGAND-METAL FRAMEWORK AND APPLICATION

(71) Applicant: Korea Atomic Energy Research Institute, Daejeon (KR)

(72) Inventors: Sung Hee Jung, Daejeon (KR); Seong-Ho Choi, Daejeon (KR); Jong Bum Kim, Daejeon (KR); Jin Ho Moon, Daejeon (KR); Min Seok Oh, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 333 days.

(21) Appl. No.: 13/714,259

(22) Filed: Dec. 13, 2012

(65) Prior Publication Data

US 2014/0005407 A1  Jan. 2, 2014

(30) Foreign Application Priority Data

Jul. 2, 2012  (KR) .................. 10-2012-0071739

(51) Int. Cl.
*C07F 1/12* (2006.01)
*C07B 59/00* (2006.01)

(52) U.S. Cl.
CPC ............... *C07F 1/12* (2013.01); *C07B 59/004* (2013.01)
USPC ...................................................... 548/101

(58) Field of Classification Search
USPC ........................................................ 548/101
See application file for complete search history.

(56) References Cited

U.S. PATENT DOCUMENTS

2007/0190326 A1 8/2007 Perry et al.
2007/0297554 A1 12/2007 Lavie et al.
2008/0193378 A1 8/2008 Comba et al.

FOREIGN PATENT DOCUMENTS

JP 2000-284096 A 10/2000
JP 2004-531875 A 10/2004
KR 10-2011-0059369 A 6/2011
KR 10-1091416 B1 12/2011
WO 2012/138379 A2 10/2012

OTHER PUBLICATIONS

Boros et al. "Acyclic Chelate with Ideal Properties for 68Ga PET Imaging Agent Elaboration" Journal of the American Chemical Society, 2010, vol. 132, pp. 15726-15733.*
Notice of Allowance dated Nov. 25, 2013 of the corresponding Korean Patent Application No. 2012-0071739, in 5 pages.
Preliminary Search Report dated Mar. 25, 2014 of the corresponding French Patent Application No. 1261702—5 pages.
Jung et al., "Synthesis and characterization of radioisotope nanospheres containing two gamma emitters", Applied Radiation and Isotopes, vol. 70, 2012, pp. 2677-2681.
Boros et al., "Acyclic Chelate with Ideal Properties for 68Ga PET Imaging Agent Elaboration", Journal American Chemical Society, 2010, vol. 132, No. 44, pp. 15726-15733.

* cited by examiner

*Primary Examiner* — Joseph Kosack
(74) *Attorney, Agent, or Firm* — Knobbe, Martens, Olson & Bear, LLP (57) ABSTRACT

This invention relates to a method of preparing a radioisotope nanostructure having a ligand-metal framework, and a radioisotope nanostructure prepared thereby. The method of preparing the radioisotope nanostructure of the invention has a simple preparation process and can thus be applied to mass production of a radioisotope nanostructure. Also, because this radioisotope nanostructure is nano-sized spherical particles and has no reactive group, it can be easily dispersed in a fluid, and this nanostructure is physically and chemically stable and thus can be utilized as a radioisotope tracer in the fields of refineries, chemistry, cement, agriculture, water resources, marine, etc. Furthermore, this nanostructure can be used for diagnosis and/or treatment in medical fields, and can be applied to checking whether a nanomaterial is harmful. In addition, this nanostructure is expected to be applicable in a variety of fields using radioisotopes.

5 Claims, 10 Drawing Sheets

|   | 2θ | d-value | intensity | FWHM |
|---|---|---|---|---|
| 1 | 8.460 | 10.4426 | 70.1 | 0.5473 |
| 2 | 16.740 | 5.6259 | 87.6 | 0.2979 |
| 3 | 38.140 | 2.3575 | 55.4 | 0.1866 |

METHOD OF PREPARING RADIOISOTOPE NANOSTRUCTURE WITH LIGAND-METAL FRAMEWORK AND APPLICATION

BACKGROUND OF THE INVENTION

1. Field of the Invention

The present invention relates to a method of preparing a radioisotope nanostructure having a ligand-metal framework, and an application thereof.

2. Description of the Related Art

Isotopes having radioactivity are referred to as radioisotopes (RI). About 300 species of natural isotopes include about 40 species of radioisotopes, most of which are isotopes of elements having atomic numbers larger than thallium. Recently, in addition to the natural radioisotopes, about 1000 species of artificial radioisotopes have been prepared, which are distributed using almost all elements. Typically, artificial radioisotopes are made by irradiating stable elements or compounds with a nuclear reactor or a particle accelerator, and are widely utilized in tracing movement of elements or compounds in materials or living bodies, investigating radiation effects on materials or organisms, serving as industrial or measuring radiation sources, performing analysis of materials using radioactivity, etc. Among these, a radioisotope used to trace the movement of elements or compounds is referred to as a radioisotope tracer. Radioisotope tracer techniques are used to achieve high-grade analysis of industrial processing related to refineries, chemistry, cement, etc., and can also lead to technological breakthroughs in the areas of the environment, medicine, agriculture, resource exploration, etc.

In order to effectively use such radioisotope tracer techniques, preparation of a radioisotope tracer is regarded as very important. Although there are slight differences depending on the application field, radioisotope tracers are required to have properties in which nuclei themselves may emit radiation and are thus converted into other kinds of nuclei, without being affected by external environments, such as pressure, temperature, chemical treatment, etc. Furthermore, in order to apply radioisotope tracers to high-temperature and/or high-pressure fluids, the tracer has to be chemically and physically stable, and should also have a density similar to that of a fluid and may thus be provided in the form of a mixture with the fluid. Typical radioisotopes, such as $^{198}$Au, $^{63}$Ni, $^{108}$Ag, $^{64}$Cu, $^{60}$Co, and so on are metals and have very high density and specific gravity compared to those of fluid media, and cannot be used in fluids for the diagnosis of industrial processing. Thus, a variety of attempts are being made to apply the radioisotope tracers to high-temperature and/or high-pressure fluids.

Korean Patent No. 10-1091416 discloses a core-shell nanostructure which is nano-sized and emits gamma rays while being stable at high temperature and high pressure, and also two-nuclide core-shell nanostructures are disclosed (J.-H. Jung, et al., Applied Radiation and Isotopes, (2012), in press). However, the core-shell nanostructures are problematic because a plurality of steps including preparation of nanoparticles, silica coating, organic treatment, neutron irradiation, and so on should be conducted, undesirably causing complicated preparation processes, and also because a long period of time is required to separate the nanoparticles from the silica coating solution using centrifugation, undesirably making it difficult to accomplish mass synthesis.

Meanwhile, a radioisotope $^{68}$Ga$^{3+}$ cation has been used as a radioisotope tracer for PET imaging by subjecting the cation to complexation with a ligand such as DOTA, NOTA, and the like and then binding the complex to a protein (E. Boros, et al., J. Am. Chem. Soc., (2010) 132: 15726-15733). However, in the case of the above ligand, coordination polymerization cannot be performed, making it impossible to prepare a spherical nanostructure suitable for high-temperature and high-pressure industrial processing environments.

As mentioned above, to effectively apply the radioisotope tracer techniques to high-temperature and high-pressure industrial processing environments, development of alternative techniques for preparing a radioisotope tracer which is physically and chemically stable and is easy to form thus enabling mass production is required.

SUMMARY OF THE INVENTION

Accordingly, the present invention has been made keeping in mind the above problems encountered in the related art, and an object of the present invention is to provide a radioisotope nanostructure which has a nano-sized spherical shape and has no reactive group and is thus physically and chemically stable and may be easily dispersed in a fluid, and a method of mass producing such a nanostructure.

However, the technical problem which is intended to be solved by the present invention is not limited to the above object, and the other objects which are not mentioned herein will be able to be apparently understood by those skilled in the art from the following description.

In order to accomplish the above object, the present invention provides a method of preparing a radioisotope nanostructure having a ligand-metal framework, comprising the step of a) preparing a radioisotope metal using neutron irradiation; b) dissolving the radioisotope metal in a solution thus obtaining a radioisotope metal ion; and c) mixing the radioisotope metal ion with an imidazole ligand.

In an embodiment of the invention, the radioisotope metal may be selected from the group consisting of $^{68}$Ga, $^{64}$Cu, $^{67}$Cu, $^{198}$Au, $^{186}$Re, $^{140}$La, $^{83}$Rb, $^{177}$Lu, $^{52}$Mn, $^{137}$Cs, $^{24}$Na, $^{46}$Sc, $^{82}$Sr, $^{85}$Sr, $^{89}$Sr, $^{241}$Am, $^{65}$Zn, $^{192}$Ir, $^{68}$Ge, $^{55}$Fe, $^{47}$Ca, $^{60}$Co, $^{57}$Cr, $^{201}$Tl, $^{99\mu}$Tc, and $^{103}$Pd.

In another embodiment of the invention, the imidazole ligand may be selected from the group consisting of 1,1'-carbonyldiimidazole, 1,1'-thiocarbonyldiimidazole, N,N'-bis(imidazole)dimethylsilane, 1,4-bis((1H-imidazol-1-yl)methyl)benzene), and 2,6-bis((1H-imidazol-1-yl)methyl)naphthalene.

In a further embodiment of the invention, the solution may be a potassium cyanide solution but is not limited thereto.

In still a further embodiment of the invention, mixing the radioisotope metal ion with the imidazole ligand may be performed at a mole ratio of the metal ion to the imidazole ligand of 1:1~1:3.

In addition, the present invention provides a radioisotope nanostructure having a ligand-metal framework, prepared using the above method.

In an embodiment of the invention, the radioisotope nanostructure may be used as a radioisotope tracer.

BRIEF DESCRIPTION OF THE DRAWINGS

The above and other objects, features, and advantages of the present invention will be more clearly understood from the following detailed description taken in conjunction with the accompanying drawings, in which.

DESCRIPTION OF SPECIFIC EMBODIMENTS

According to the present invention, a method of preparing a radioisotope nanostructure having a ligand-metal framework includes a) preparing a radioisotope metal using neutron irradiation, b) dissolving the radioisotope metal in a solution to prepare a radioisotope metal ion, and c) mixing the radioisotope metal ion with an imidazole ligand.

Figure 1:
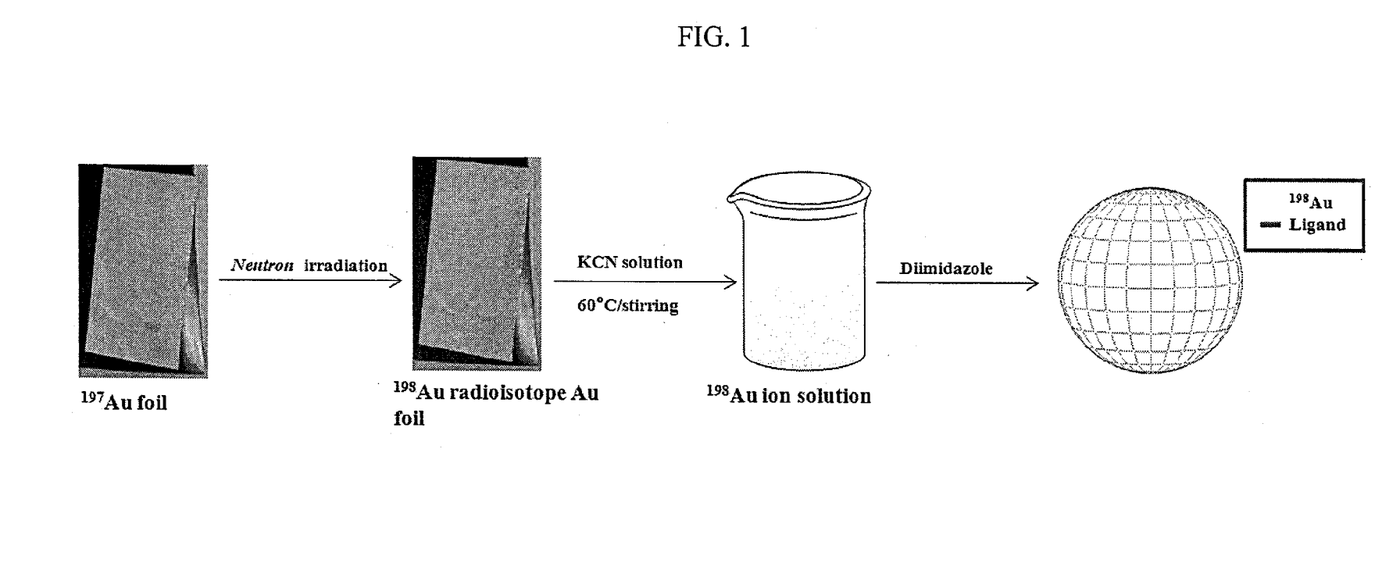
FIG. 1 schematically illustrates a process of preparing a radioisotope nanostructure having a ligand-metal framework.

Typically, in a metal complex, a ligand bond is formed depending on the type of metal ion. Thus, as illustrated in FIG. 1, a metal is irradiated with neutrons emitted from an experimental reactor to prepare a radioisotope metal, which is then dissolved in the solution, thus obtaining the radioisotope metal ion. The kind of solution is not limited so long as it may dissolve the radioisotope metal, and a potassium cyanide solution is particularly useful.

The kind of radioisotope metal is not limited so long as it is a metal isotope having radioactivity, and is preferably selected from the group consisting of $^{68}$Ga, $^{64}$Cu, $^{67}$Cu, $^{198}$Au, $^{186}$Re, $^{140}$La, $^{83}$Rb, $^{177}$Lu, $^{52}$Mn, $^{137}$Cs, $^{24}$Na, $^{46}$Sc, $^{82}$Sr, $^{85}$Sr, $^{89}$Sr, $^{241}$Am, $^{65}$Zn, $^{192}$Ir, $^{68}$Ge, $^{55}$Fe, $^{47}$Ca, $^{60}$Co, $^{57}$Cr, $^{201}$Tl, $^{99\mu}$Tc, and $^{103}$Pd. Also, dissolving the radioisotope metal in a 1 M potassium cyanide solution may be performed while stirring at 60° C. in order to increase the solubility of the radioisotope metal, but the present invention is not limited thereto. Because the concentration at which the radioisotope metal may dissolve in the potassium cyanide solution may vary depending on the temperature and the time, the concentration ratio of the potassium cyanide solution and the radioisotope metal is not limited so long as the radioisotope metal is completely dissolved.

Subsequently, mixing the prepared metal ion with the imidazole ligand is performed so that a complexation reaction takes place, thus affording a radioisotope nanostructure having a ligand-metal framework. The kind of imidazole ligand is not limited so long as it has a benzene ring, and is preferably selected from the group consisting of 1,1'-carbonyldiimidazole, 1,1'-thiocarbonyldiimidazole, N,N'-bis(imidazole)dimethylsilane, 1,4-bis((1H-imidazol-1-yl)methyl)benzene, and 2,6-bis((1H-imidazol-1-yl)methyl) naphthalene. Also, mixing the radioisotope metal ion with the imidazole ligand may be carried out at a mole ratio of the metal ion to the imidazole ligand of 1:1~1:3, but the present invention is not limited thereto.

In an embodiment of the invention, the nanostructure prepared using the above method was analyzed to be nano-sized and spherical and to have a ligand-metal framework (Example 4). Furthermore, because the prepared nanostructure having a ligand-metal framework results from using a metal, which is not a synthetic material, and an organic compound ligand having a benzene ring as a fundamental skeleton, it is stable at high temperature and/or high pressure.

Thus, the present invention provides a radioisotope nanostructure having a ligand-metal framework prepared using the above method. This nanostructure may be used as a radioisotope tracer but is not limited thereto.

Better understanding of the present invention may be obtained from the following examples. However, such examples are set forth to illustrate, but are not to be construed as limiting the present invention.

EXAMPLE

Example 1

Synthesis of Imidazole Ligand

Figure 2:
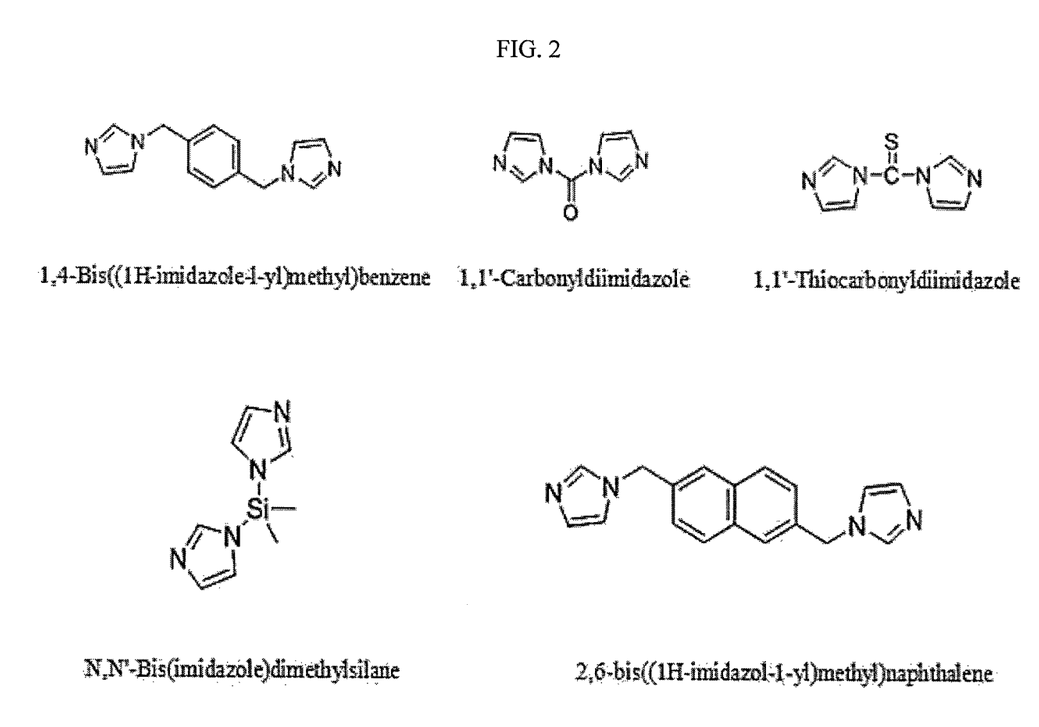
FIG. 2 illustrates the chemical formulas of imidazole ligands used in the present invention.

The chemical formulas of imidazole ligands which will be bound to the radioisotope are illustrated in FIG. 2. Among these imidazole ligands, 1,1'-carbonyldiimidazole, 1,1'-thiocarbonyldiimidazole, and N,N'-bis(imidazole)dimethylsilane are commercially available, and 1,4-bis((1H-imidazol-1-yl)methyl)benzene and 2,6-bis((1H-imidazol-1-yl)methyl) naphthalene were directly synthesized because they could not be purchased commercially.

In order to synthesize 1,4-bis((1H-imidazol-1-yl)methyl)benzene, the following procedures were conducted. Specifically, 100 ml of DMF and 680 mg of 10 mmol imidazole were added into a 250 ml reactor, and the resulting solution was mixed with 440 mg of NaH (60% in oil, 11 mmol) and stirred at room temperature for 2 hr, and thereby hydrogen ($H_2$) gas was generated, and a colorless solution tuned to a light yellow color, thus obtaining a sodium-substituted imidazole salt. This solution was then mixed with 0.88 g of a,a'-dichloro-p-xylene (5 mmol) and reacted until the xylene was completely dissolved, followed by performing vacuum drying to remove the DMF solvent. The dried imidazole salt was mixed with dichloromethane (MC) and distilled water, and the solvent of the separated organic layer was removed, thus synthesizing an organic imidazole ligand which was then ascertained by nuclear magnetic resonance (NMR). The results are given below.

$^1$H NMR (ppm): CH 7.74 imidazole, CH 7.11 1-benzene, CH2 5.46 methylene FT-IR: 3200 cm$^{-1}$ Aromatic C—H (broad Peak), 2700 cm$^{-1}$ C—H, GC-MAss (FID): m/z: 238.12

In order to synthesize 2,6-bis((1H-imidazol-1-yl)methyl) naphthalene, the following procedures were conducted. Specifically, a 250 ml reactor was provided in an ice bath, 100 ml of dichloromethane (MC) was added, and the resulting solution was mixed with 0.2 g of 2,6-bis(hydroxymethyl) naphathalene (1 mmol) and 0.012 ml of thionyl chloride (1 mmol) and stirred for 2 hr. The stirred solution was placed in a separatory funnel along with distilled water to separate an organic layer, which was then completely dissolved with the addition of 100 ml of a dichloromethane (MC) solvent. The dissolved solution was mixed with 0.014 mg of imidazole (2 mmol) and stirred for 2 hr, after which the solvent was removed, thus synthesizing an organic imidazole ligand, which was then ascertained by NMR. The results are given below.

$^1$H NMR (ppm): CH 7.74 imidazole, CH 7.47 2-naphthalene, CH2 5.46 methylene, FT-IR: 3200 cm$^{-1}$ Aromatic (triple peak) C—H, 2700 cm C—H, GC-MAss (FID): m/z: 288.14.

Example 2

Preparation of Radioisotope KAuCN$_2$ Solution

To prepare a radioisotope 1.0 M KAuCN$_2$ solution, 17 mg of a gold foil ($^{197}$Au) was irradiated with neutrons emitted from an experimental reactor thus forming a radioisotope $^{198}$Au foil, after which 17 mg of the radioisotope $^{198}$Au foil was reacted with a 1.0 M potassium cyanide (KCN) solution at 60° C., thus obtaining a 1.0 M KAuCN$_2$ solution.

Example 3

Preparation of Radioisotope Nanostructure Having Ligand-Metal Framework

To prepare a radioisotope tracer, a radioisotope nanostructure having a ligand-metal framework was manufactured. The imidazole ligands prepared in Example 1 were respectively dissolved in ethanol, slowly added to the radioisotope 1.0 M KAuCN$_2$ solution of Example 3, and stirred at 3,000~4,000 rpm so that coordination polymerization took place, thereby obtaining a radioisotope nanostructure. The method of preparing the radioisotope nanostructure having a ligand-metal framework is schematically shown in FIG. 1.

Example 4

Analysis of Properties of the Radioisotope Nanostructure Having Ligand-Metal Framework 4-1. Analysis of the Radioisotope Nanostructure Using Particle Size Distribution Analyzer To analyze the size of the radioisotope nanostructure having a ligand-metal framework of Example 3, the radioisotope nanostructure dispersed in the ethanol/water solvent mixture was analyzed using a particle size distribution analyzer (an electrophoretic light scattering spectrophotometer (ELS)). The results are shown in FIG. 3.

Figure 3:
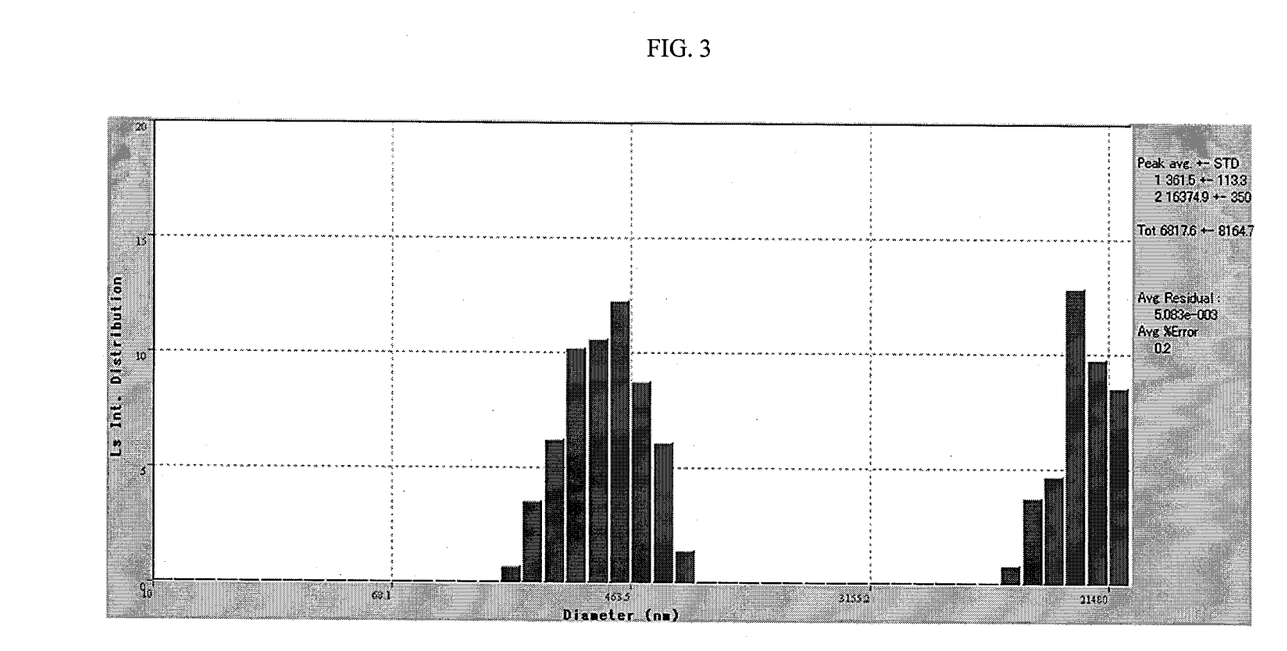
FIG. 3 illustrates the results for the radioisotope nanostructure ascertained using a particle size distribution analyzer.

As shown in FIG. 3, the radioisotope nanostructure had an average diameter of 200~300 nm except a portion where agglomeration occurred (about a size of 2000 nm).

4-2. Analysis of the Radioisotope Nanostructure Using Optical Microscope

To ascertain the radioisotope nanostructure having a ligand-metal framework of Example 3, the radioisotope nanostructure dispersed in the ethanol/water solvent mixture was observed using an optical microscope (OM). The results are shown in FIG. 4.

Figure 4:
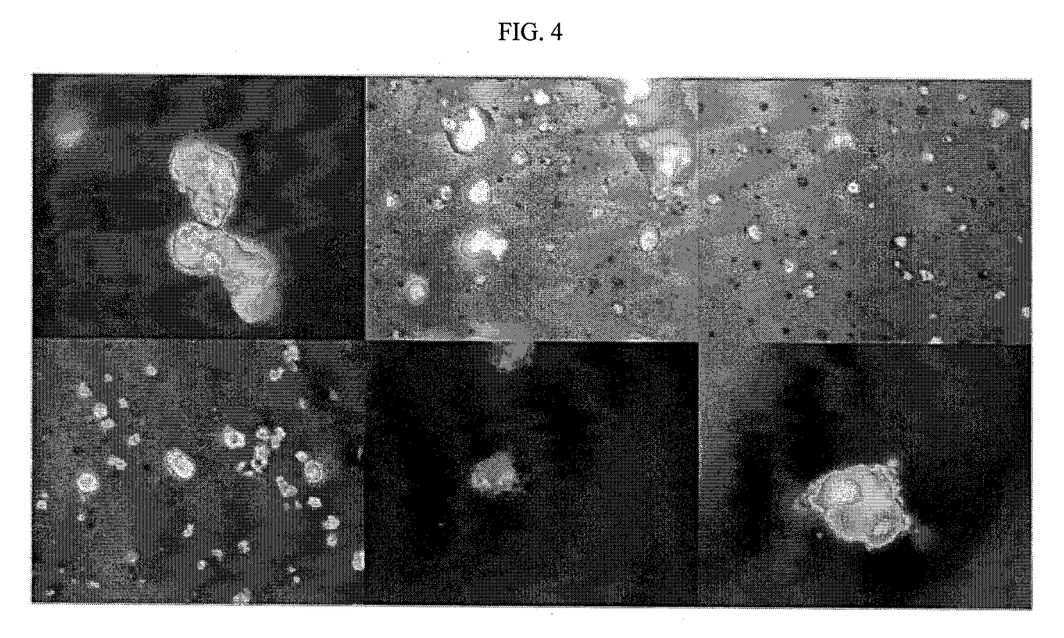
FIG. 4 illustrates the results for the radioisotope nanostructure ascertained using an optical microscope.

As shown in FIG. 4, the radioisotope nanostructure emitted light, from which a metal was evaluated to be contained therein.

4-3. Analysis of the Radioisotope Nanostructure Using Scanning Electron Microscope To ascertain the radioisotope nanostructure having a ligand-metal framework of Example 3, the dried radioisotope nanostructure was observed using a scanning electron microscope (SEM). The results are shown in FIG. 5.

Figure 5:
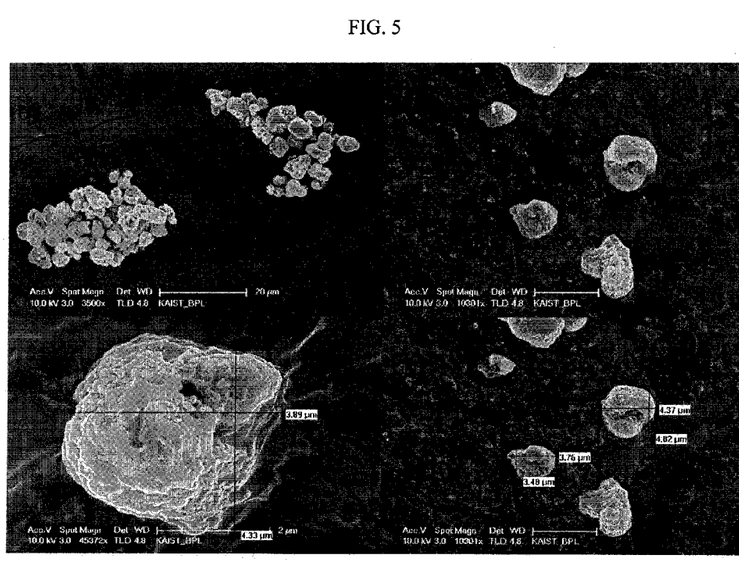
FIG. 5 illustrates the results for the radioisotope nanostructure ascertained using a scanning electron microscope.

As shown in FIG. 5, the radioisotope nanostructure had a spherical shape with an average diameter of about 3 μm, from which, because of the properties of the metal contained in the radioisotope nanostructure having a ligand-metal framework, agglomeration was evaluated to occur in the course of removing the solvent.

4-4. Analysis of the Radioisotope Nanostructure Using Transmission Electron Microscope and Energy Dispersive Analyzer To ascertain the radioisotope nanostructure having a ligand-metal framework of Example 3, the radioisotope nanostructure was observed using a transmission electron microscope (TEM) and an energy dispersive analyzer (energy dispersive X-ray fluorescence spectroscopy (EDAX)). The results are shown in FIGS. 6 and 7.

Figure 6:
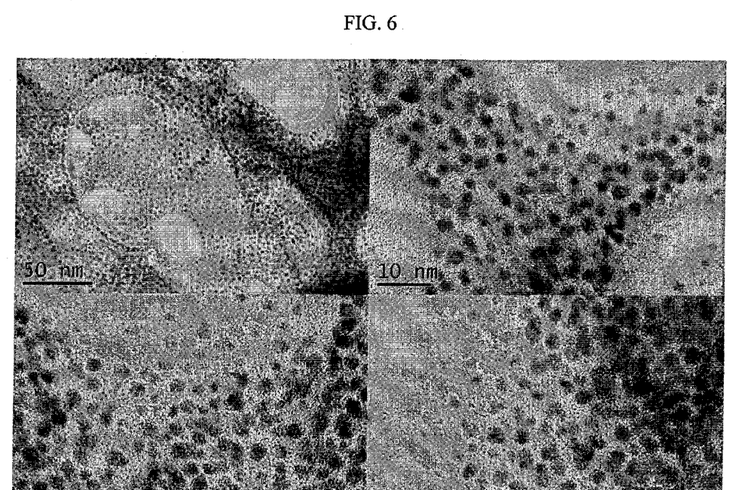
FIG. 6 illustrates the results for the radioisotope nanostructure ascertained using a transmission electron microscope.
Figure 7:
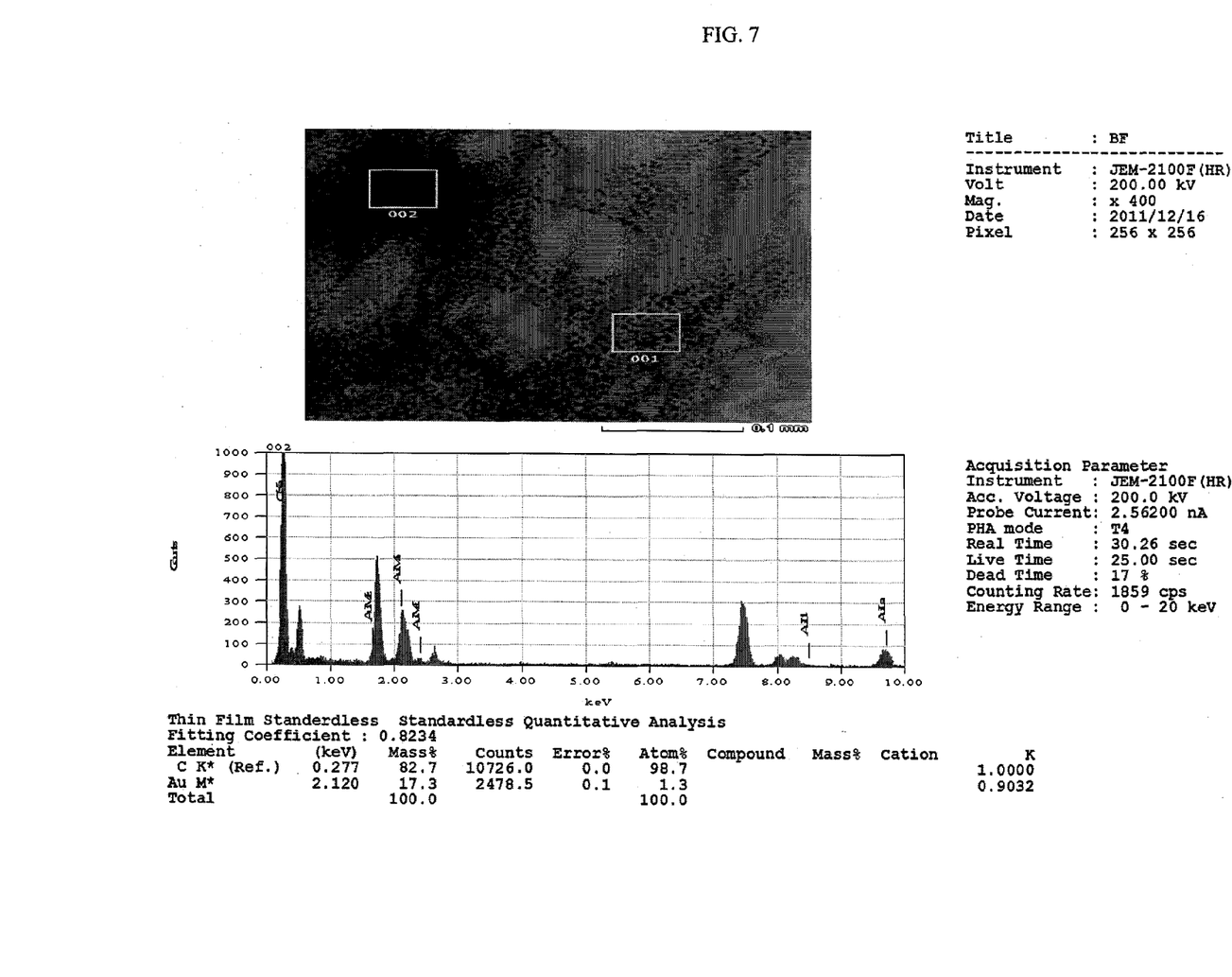
FIG. 7 illustrates the results for the radioisotope nanostructure ascertained using an energy dispersive analyzer.

As shown in FIG. 6, a 10 nm or less sized spherical radioisotope nanostructure having a ligand-metal framework was prepared. Also, as illustrated in FIG. 7, gold was contained in the nanostructure. Thereby, the spherical radioisotope nanostructure having a ligand-metal framework can be confirmed to be successfully obtained.

4-5. Analysis of the Radioisotope Nanostructure Using X-Ray Diffraction

To ascertain the radioisotope nanostructure having a ligand-metal framework of Example 3, the radioisotope nanostructure was analyzed using X-ray diffraction (XRD). The results are shown in FIG. 8.

Figure 8:
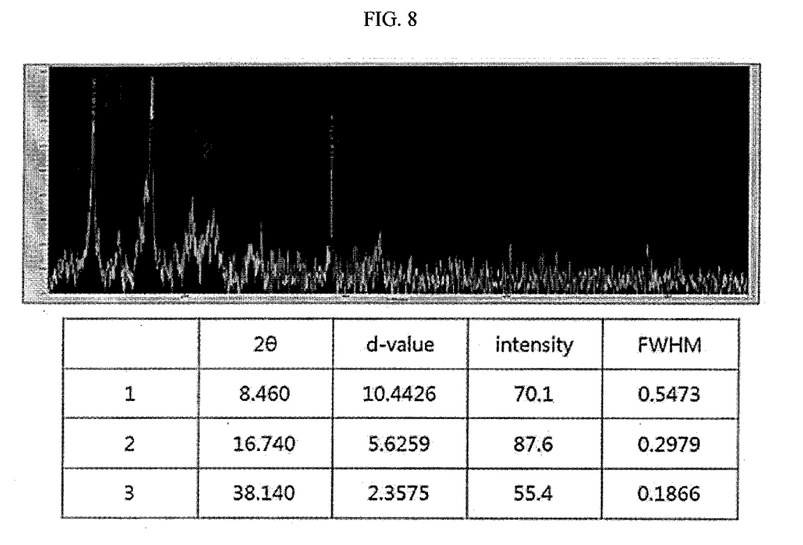
FIG. 8 illustrates the results for the radioisotope nanostructure ascertained using X-ray diffraction.

As shown in FIG. 8, in the results of 2θ and d-values for the peaks corresponding to Nos. 1, 2, and 3, it can be seen that the peak corresponding to a specific element was not observed via the d-values using element emission methods for specific elements, from which the product was evaluated to be in a structure or polymer state, and thereby resulted in a radioisotope nanostructure having a ligand-metal framework.

4-6. Analysis of the Radioisotope Nanostructure Using Thermogravimetric Analyzer To ascertain the radioisotope nanostructure having a ligand-metal framework of Example 3, the radioisotope nanostructure was observed using a thermogravimetric analyzer (TGA). The results are shown in FIG. 9.

Figure 9:
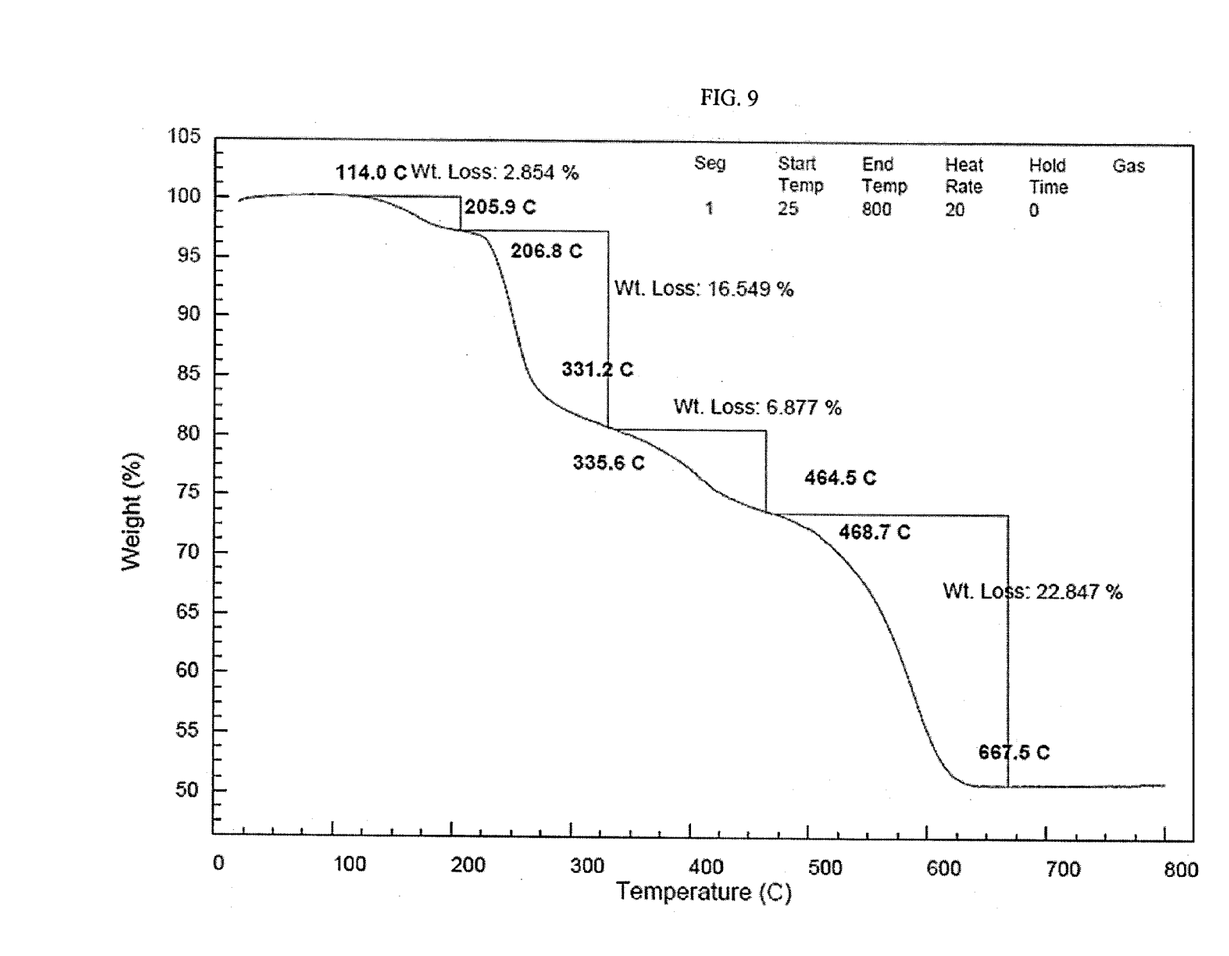
FIG. 9 illustrates the results for the radioisotope nanostructure ascertained using a thermogravimetric analyzer.

As shown in FIG. 9, weight loss began to occur starting from about 114° C., and the maximum loss took place at 667.5° C., and then the weight was maintained. The maximum weight loss was about 49%, and the non-lost 50% was obtained by the gold component. Thereby, the radioisotope nanostructure can be confirmed to be stable to heat.

Figure 10:
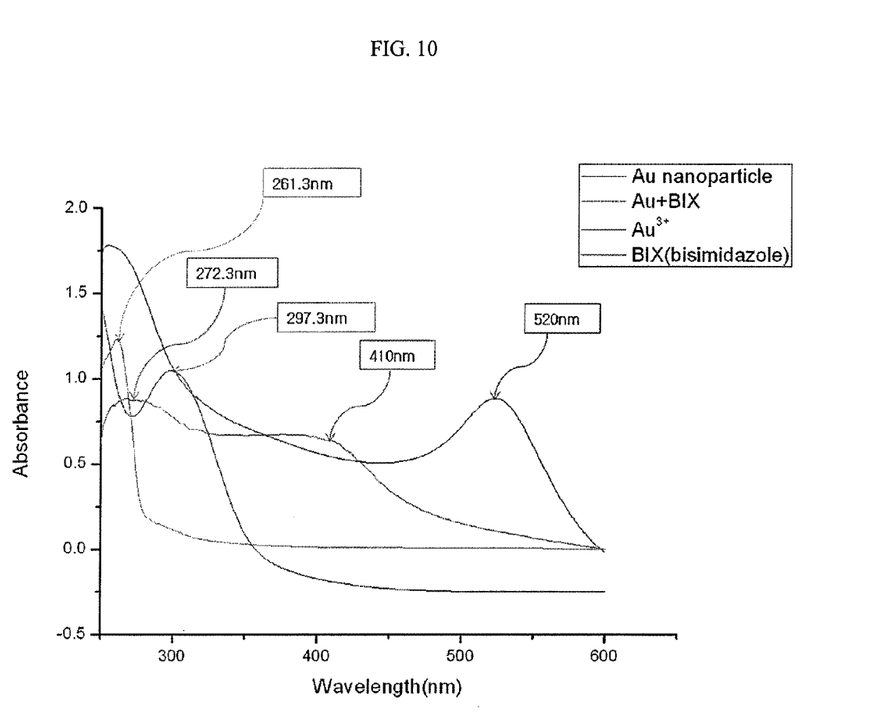
FIG. 10 illustrates the results for the radioisotope nanostructure ascertained using a UV-visible spectrophotometer.

4-7. Analysis of the Radioisotope Nanostructure Using UV-Visible Spectrophotometer To ascertain the radioisotope nanostructure having a ligand-metal framework of Example 3, the UV spectrum of the radioisotope nanostructure was observed using a UV-visible spectrophotometer. The results are shown in FIG. 10.

4-8. Analysis of the Radioisotope Nanostructure Using Neutron Activation Analyzer To ascertain the radioisotope nanostructure having a ligand-metal framework of Example 3, the radioisotope nanostructure was irradiated with neutrons using a neutron activation analyzer (HPGe detector, NAA, 25% relative efficiency, FWHM 1.85 keV at 1170, 1332 keV of $^{60}$Co) and the gamma-ray spectrum thereof was then analyzed. The results are shown in FIG. 11.

Figure 11:
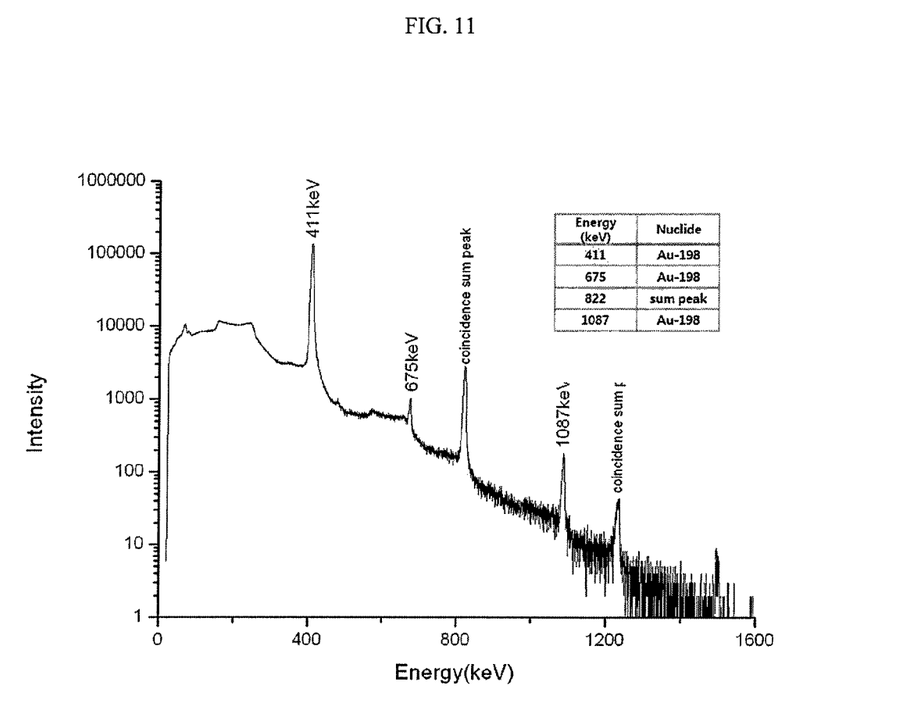
FIG. 11 illustrates the results for the radioisotope nanostructure ascertained using a neutron activation analyzer.

As shown in FIG. 11, $^{198}$Au is an isotope having gamma-ray energy of 412 KeV at a minimum and 1087 KeV at a maximum, and the radioisotope nanostructure having a ligand-metal framework can be confirmed to be successfully prepared via the gamma-ray spectrum.

As described hereinbefore, the present invention provides a method of preparing a radioisotope nanostructure having a ligand-metal framework and an application thereof. According to the present invention, the method of preparing a radioisotope nanostructure having a ligand-metal framework has a simple preparation process and can thus be applied to mass production of a radioisotope nanostructure. Also, because the radioisotope nanostructure prepared using the above method is nano-sized spherical particles and has no reactive group, it can be easily dispersed in a fluid, and as well this nanostructure is physically and chemically stable and thus can be utilized as a radioisotope tracer in the fields of refineries, chemistry, cement, agriculture, water resources, marine, etc. Furthermore, this nanostructure can be used for diagnosis and/or treatment in medical fields, and can be applied to checking whether a nanomaterial is harmful. In addition, the particle size of the nanostructure is adjusted during the preparation process, and thereby this nanostructure can be widely employed in imaging measurement and other industrial uses. For example, there are illustrated water pollution prevention, standardization of nuclear technology for diagnosing and treating livestock diseases, measurement of radiation using a gamma camera to achieve livestock disease eradication, use of alternative irradiation techniques such as X-rays, electronic beams, etc. in food investigation, and analysis of specific radioisotopes to identify serious soil erosion areas in soil and land use.

Although the preferred embodiments of the present invention have been disclosed for illustrative purposes, those skilled in the art will appreciate that various modifications, additions, and substitutions are possible, without departing from the scope and spirit of the invention as disclosed in the accompanying claims.

What is claimed is:

1. A method of preparing a radioisotope nanostructure having a ligand-metal framework, comprising the steps of:
    a) preparing a radioisotope metal using neutron irradiation;
    b) dissolving the radioisotope metal in a solution thus obtaining a radioisotope metal ion; and
    c) mixing the radioisotope metal ion with an imidazole ligand.

2. The method of claim 1, wherein the radioisotope metal is selected from the group consisting of $^{68}$Ga, $^{64}$Cu, $^{67}$Cu, $^{198}$Au, $^{186}$Re, $^{140}$La, $^{83}$Rb, $^{177}$Lu, $^{52}$Mn, $^{137}$Cs, $^{24}$Na, $^{46}$Sc, $^{82}$Sr, $^{85}$Sr, $^{89}$Sr, $^{241}$Am, $^{65}$Zn, $^{192}$Ir, $^{68}$Ge, $^{55}$Fe, $^{47}$Ca, $^{60}$Co, $^{57}$Cr, $^{201}$Tl, $^{99m}$Tc, and $^{103}$Pd.

3. The method of claim 1, wherein the imidazole ligand is selected from the group consisting of 1,1'-carbonyldiimidazole, 1,1'-thiocarbonyldiimidazole, N,N'-bis(imidazole)dimethylsilane, 1,4-bis((1H-imidazol-1-yl)methyl)benzene), and 2,6-bis((1H-imidazol-1-yl)methyl) naphthalene.

4. The method of claim 1, wherein the solution is a potassium cyanide solution.

5. The method of claim 1, wherein the mixing the radioisotope metal ion with the imidazole ligand is performed at a mole ratio of the metal ion to the imidazole ligand of 1:1~1:3.

* * * * *